US008610077B2

(12) United States Patent
Beaulieu et al.

(10) Patent No.: US 8,610,077 B2
(45) Date of Patent: Dec. 17, 2013

(54) FLUENCE MONITORING DEVICES WITH SCINTILLATING FIBERS FOR X-RAY RADIOTHERAPY TREATMENT AND METHODS FOR CALIBRATION AND VALIDATION OF SAME

(75) Inventors: Luc Beaulieu, Quebec (CA); Luc Gingras, Quebec (CA); Mathieu Goulet, Quebec (CA)

(73) Assignee: Universite Laval, Quebec, Quebec (CA)

( * ) Notice: Subject to any disclaimer, the term of this patent is extended or adjusted under 35 U.S.C. 154(b) by 207 days.

(21) Appl. No.: 13/207,624

(22) Filed: Aug. 11, 2011

(65) Prior Publication Data

US 2012/0205530 A1    Aug. 16, 2012

Related U.S. Application Data

(60) Provisional application No. 61/375,125, filed on Aug. 19, 2010.

(51) Int. Cl.
*G01D 18/00* (2006.01)
*G01T 1/20* (2006.01)

(52) U.S. Cl.
USPC .......................... 250/367; 250/252.1; 250/368

(58) Field of Classification Search
USPC .......... 250/252.1, 361 R, 362, 366, 367, 368, 250/369, 370.09
See application file for complete search history.

(56) References Cited

U.S. PATENT DOCUMENTS

| | | | | |
|---|---|---|---|---|
| 5,856,673 A | * | 1/1999 | Ikegami et al. | 250/368 |
| 5,905,263 A | * | 5/1999 | Nishizawa et al. | 250/368 |
| 6,066,851 A | * | 5/2000 | Madono et al. | 250/367 |
| 6,087,666 A | * | 7/2000 | Huston et al. | 250/484.5 |
| 2006/0017009 A1 | * | 1/2006 | Rink et al. | 250/484.5 |
| 2006/0027756 A1 | * | 2/2006 | Thomson et al. | 250/370.07 |
| 2009/0014665 A1 | * | 1/2009 | Fleming et al. | 250/484.5 |
| 2010/0127177 A1 | * | 5/2010 | Schmitt et al. | 250/362 |
| 2011/0035151 A1 | * | 2/2011 | Botto | 702/2 |
| 2012/0032087 A1 | * | 2/2012 | Sugihara | 250/367 |

FOREIGN PATENT DOCUMENTS

WO    WO 2010/057500 A1    5/2010

OTHER PUBLICATIONS

"DAVID—a translucent multi-wire transmission ionization chamber for in vivo verification of IMRT and conformal irradiation techniques", B. Poppe et al, Physics in Medicine and Biology, vol. 51, pp. 1237-1248, published Feb. 15, 2006.

* cited by examiner

*Primary Examiner* — Mark R Gaworecki
(74) *Attorney, Agent, or Firm* — Bereskin & Parr LLP

(57) ABSTRACT

According to one aspect, a fluence monitoring detector for use with a multileaf collimator on a radiotherapy machine having an x-ray radiation source. The fluence monitoring detector includes a plurality of scintillating optical fibers, each scintillating optical fiber configured to generate a light output at each end thereof in response to incident radiation pattern thereon from the radiation source and multileaf collimator, a plurality of collection optical fibers coupled to the opposing ends of the scintillating optical fibers and operable to collect the light output coming from both ends of each scintillating optical fiber, and a photo-detector coupled to the collection optical fibers and operable to converts optical energy transmitted by the collection optical fibers to electric signals for determining actual radiation pattern information.

23 Claims, 9 Drawing Sheets a) SLE
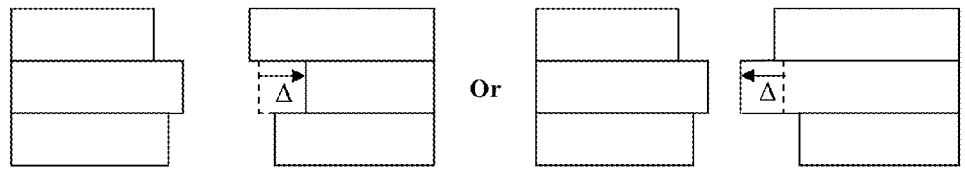
b) PTE
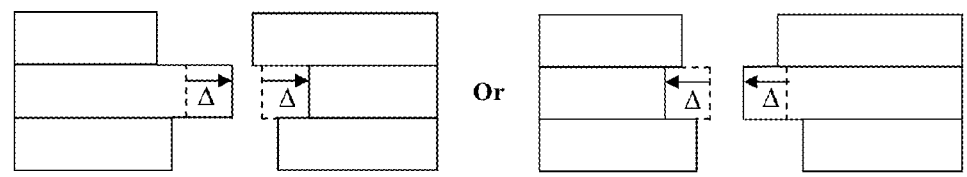
c) LBE
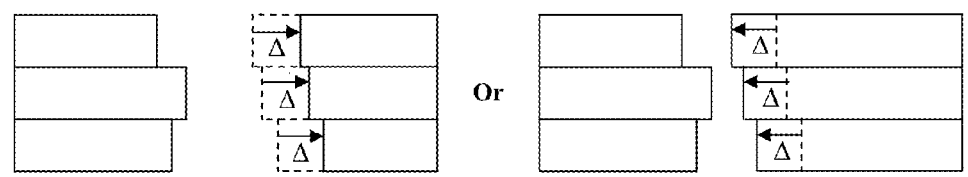
d) FTE
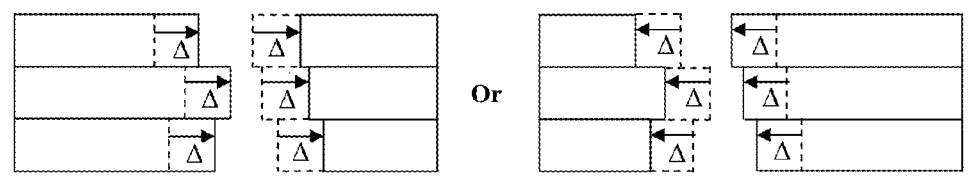
Figure 8

Table 1: Deviations observed in the central position of the radiation field on the fiber ($x_c$) and the integral fluence passing through the detector ($\Phi_{int}$) between modified (random error included) and error-free segments of selected step-and-shoot head and neck IMRT fields.

a) Deviations observed for a single leaf error (SLE)

| Δ (mm) | Deviation of $x_c$ (SD[1]) | | | Δ (mm) | Deviation of $\Phi_{int}$ (%) | | |
|---|---|---|---|---|---|---|---|
| | Unmodified leaves | | Modified leaves (mean) | | Unmodified leaves | | Modified leaves (mean) |
| | Max | Mean | | | Max | Mean | |
| 2 | | | 1.8 | 1 | | | 1.3 |
| 3 | 2.6 | 0.14 | 2.7 | 2 | 0.21 | 0.01 | 2.6 |
| 4 | | | 3.7 | 3 | | | 3.9 | b) Deviations observed for a pair translation error (PTE)

| Δ (mm) | Deviation of $x_c$ (SD[1]) | | | Δ (mm) | Deviation of $\Phi_{int}$ (%) | | |
|---|---|---|---|---|---|---|---|
| | Unmodified leaves | | Modified leaves (mean) | | Unmodified leaves | | Modified leaves (mean) |
| | Max | Mean | | | Max | Mean | |
| 2 | | | 4.1 | 2 | | | 0.35 |
| 4 | 2.3 | 0.43 | 10.1 | 6 | 0.27 | -0.04 | 1.5 |
| 6 | | | 15.3 | 10 | | | 2.6 | c) Deviations observed for a single leaf bank error (LBE)

| Δ (mm) | Deviation of $x_c$ (SD[1]) Modified leaves (mean) | Δ (mm) | Deviation of $\Phi_{int}$ (%) Modified leaves (mean) |
|---|---|---|---|
| 1 | 1.4 | 1 | 1.5 |
| 2 | 3.0 | 2 | 3.4 |
| 3 | 5.1 | 3 | 5.2 | d) Deviations observed for a field translation error (FTE)

| Δ (mm) | Deviation of $x_c$ (SD[1]) Modified leaves (mean) | Δ (mm) | Deviation of $\Phi_{int}$ (%) Modified leaves (mean) |
|---|---|---|---|
| 1 | 3.3 | 1 | 0.4 |
| 2 | 6.3 | 3 | 0.6 |
| 3 | 9.5 | 5 | 0.5 |

[1]Errors given in number of standard deviation (as calculated using Poisson statistics)
Dose on the fiber for each segment: 11 to 14 cGy. Length of fiber irradiated: 0.5 to 5 cm.

Figure 9

FLUENCE MONITORING DEVICES WITH SCINTILLATING FIBERS FOR X-RAY RADIOTHERAPY TREATMENT AND METHODS FOR CALIBRATION AND VALIDATION OF SAME

RELATED APPLICATIONS

This application claims the benefit of U.S. Provisional patent application Ser. No. 61/375,125 filed Aug. 19, 2010 and entitled FLUENCE MONITORING DEVICES WITH SCINTILLATING FIBERS FOR X-RAY RADIO-THERAPY TREATMENT AND METHODS FOR CALIBRATION AND VALIDATION OF SAME, the entire contents of which are hereby incorporated by reference herein for all purposes.

FIELD

The embodiments described herein relate to the field of x-ray radiation treatment, and in particular to fluence monitoring devices with scintillating fibers, and validation methods for verification of the delivery and conformity of x-ray radiation dose patterns using such fluence monitoring devices.

INTRODUCTION

Radiation therapy, or "radiotherapy", is the medical use of ionizing radiation to control malignant cells in cancer treatments. Most frequently, radiation therapy makes use of x-ray beams originating from outside the patient body (i.e. external x-ray radiotherapy). Many of the most advanced modes of treatment in external x-ray radiotherapy make intensive use of multi-leaf collimators (MLC) to adequately shape the x-ray beams used for a particular treatment.

Each MLC may have a number of movable leaves (generally made of a metal such as tungsten or another high atomic number material) that are placed under the x-ray beam to block at least a part of the incident fluence pattern and modulate the intensity profile of the x-ray beam. These advanced modalities of treatment (such as intensity modulated radiation therapy (IMRT), intensity modulated arc therapy (IMAT), or stereotactic body radiotherapy (SBRT)) are inherently more complex in planning, delivery and software/hardware communication than their static counterparts, and are often subject to delivery and leaf positioning errors.

As these advanced treatment modalities use complex combinations of often small and irregular field shapes to produce conformal radiation dose distributions at a treatment region (e.g. a tumor site), a leaf positioning error of only a few millimeters can have dire repercussions on the actual dose delivered, greatly impacting the quality of the treatment. Large deviations from the planned treatment can lead to significant under-dosage or over-dosage, and may result in severe injury to a patient or even death.

Furthermore, the development of adaptive radiation therapy procedures has resulted in an increased need for real-time quality control. For example, adaptive protocols may modify the MLC field shapes' and dose contribution in-use, or just before use (e.g. while treatment is underway or about to be delivered). Typical, off-line quality assurance protocols are currently inadequate to assess the quality of such treatment procedures. As a result, the inventors have identified a need for improved verification and quality control devices for x-ray radiation delivery systems.

SUMMARY

According to one aspect, there is provided a fluence monitoring detector for use with a multileaf collimator on a radiotherapy machine having an x-ray radiation source, the fluence monitoring detector comprising a plurality of scintillating optical fibers, each scintillating optical fiber configured to generate a light output at each end thereof in response to incident radiation pattern thereon from the radiation source and multileaf collimator, a plurality of collection optical fibers coupled to the opposing ends of the scintillating optical fibers and operable to collect the light output coming from both ends of each scintillating optical fiber, and a photo-detector coupled to the collection optical fibers and operable to converts optical energy transmitted by the collection optical fibers to electric signals for determining actual radiation pattern information. The scintillating fibers may be embedded in a phantom slab. The phantom slab may be made of a material with properties relative to radiation that are similar to the material used in the scintillating optical fibers.

Each pair of leaves in the multileaf collimator may be associated with a particular scintillating optical fiber. Each scintillating optical fiber may be arranged parallel to a direction of motion of the leaves of the multileaf collimator. Each scintillating optical fibers may be positioned underneath a pair of leaves of the multileaf collimator. Each scintillating optical fiber may have a length selected so as to span the maximum leaf span of a pair of leaves in the multileaf collimator.

The scintillating optical fibers may be located on the opposite side of the multileaf collimator from the radiation source.

The scintillating optical fibers may be located close enough to the opposite side of the multileaf collimator from the radiation source as to keep necessary clearance between the patient and the scintillating optical fibers.

The scintillating optical fibers may be thin enough so that one scintillating optical fiber can monitor the fluence pattern associated with one leaf pair of the multileaf collimator.

In some embodiments, both the scintillating fiber length and the phantom slab area are large enough to span the maximum leaf span of the multileaf collimator.

In some embodiments, both the scintillating fiber and the phantom slab assembly are thin enough as to minimize the attenuation of the incoming radiation beam.

The total number of scintillating optical fibers may be equivalent to the number of leaf pairs in the multi-leaf collimator.

The light collected by each end of each scintillating optical fiber may be determined by the integration of the contribution of each infinitesimal element along that fiber according to the following equation:

$$I_{\pm} = C_{\pm} \cdot \int_{-\frac{L}{2}}^{\frac{L}{2}} \kappa(x) \cdot \Phi_l(x) \cdot e^{\pm \lambda(x)} \cdot dx$$

where $\kappa(x)$ represents the scintillation efficiency, $\Phi_l(x)$ represents the linear fluence across the fiber $(m^{-1})$, $\lambda(x)$ accounts for the differential light attenuation along the optical fiber, $C_{\pm}$ represent the light losses due to the optical coupling to the photo-detector and L represent the fiber length.

The photo-detector may be further configured to determine actual radiation pattern information, and compare this actual radiation pattern information to the expected radiation pattern to determine how closely the actual radiation pattern matches the expected radiation pattern.

The detector may further comprise several solid slabs located under the scintillating fiber array and the phantom slab.

According to another aspect there is provided a method of calibrating a fluence monitoring detector that has scintillating optical fibers for use with a multileaf collimator on a radiotherapy machine having an x-ray radiation source, the method comprising using a narrow rectangular radiation field incident on the scintillating optical fibers, with the scintillating optical fibers set perpendicular to the rectangular field and the radiation field is wide enough to enable simultaneous irradiation of all the fibers, and determining the light collected by each end of the scintillating fibers according to the following equation:

$$I_\pm = C_\pm \cdot \kappa(x_0) \cdot \Phi_{int}(x_0) \cdot e^{\pm \lambda(x_0)} \quad x_0 \in \left[x_f - \frac{d}{2}, x_f + \frac{d}{2}\right]$$

wherein d represents the effective rectangular field width (that is, the width beyond which the radiation fluence is considered to be negligible) and $x_0$ represents the effective point of measure, as defined by the integral mean value theorem, $\kappa(x)$ represents the scintillation efficiency, $\Phi_l(x)$ represents the linear fluence across the fiber ($m^{-1}$), $\lambda(x)$ accounts for the differential light attenuation along the optical fiber, and $C_\pm$ represent the light losses due to the optical coupling to the photo-detector.

The method may further comprise determining the values of $\kappa(x)$ and $\lambda(x)$ at the position $x_f$ on the fibers according to the following equations:

$$\mu(x_f) = \frac{1}{2} \ln\left(\frac{I_+(x_f)}{I_-(x_f)} \cdot \frac{I_-(0)}{I_+(0)}\right)$$

$$\frac{\kappa(x_f)}{\kappa(0)} = \sqrt{\frac{I_+(x_f)}{I_+(0)} \cdot \frac{I_-(x_f)}{I_-(0)}}$$

The method may further comprise applying the rectangular radiation field over the entire scintillating optical fiber length in a plurality of irradiations in order to calculate $\mu(x)$ and $\kappa(x)$ for all positions along the fiber.

According to another aspect, there is provided a method of validation of an incident radiation pattern on an array of scintillating optical fibers for use with a multileaf collimator on a radiotherapy machine having an x-ray radiation source, comprising calculating the following field parameters: central position of the radiation interaction on the scintillation optical fiber ($x_c$) and the integral of the fluence passing through the scintillating optical fiber ($\phi_{int}$) according to the following equations:

$$x_c = \frac{1}{2\mu} \ln\left(\frac{I_+}{I_{N+}} \cdot \frac{I_{N-}}{I_-}\right)$$

$$\Phi_{int} = \Phi_{intN} \sqrt{\frac{I_+}{I_{N+}} \cdot \frac{I_-}{I_{N-}}}$$

wherein $\mu$ is a constant that represents the mean attenuation coefficient of the scintillating optical fibers, and wherein $I_+$, $I_-$, $I_{N+}$ and $I_{N-}$ are defined by the following equation:

$$I_\pm = C_\pm \cdot \int_{-\frac{L}{2}}^{\frac{L}{2}} \kappa(x) \cdot \Phi_l(x) \cdot e^{\pm \lambda(x)} \cdot dx$$

where $\kappa(x)$ represents the scintillation efficiency, $\Phi_l(x)$ represents the linear fluence across the fiber ($m^{-1}$), $\lambda(x)$ accounts for the differential light attenuation along the optical fiber, $C_\pm$ represent the light losses due to the optical coupling to the photo-detector and L represent the fiber length.

In some embodiments of the method of validation, $I_+$ and $I_-$ are for the field under analysis and $I_{N+}$ and $I_{N-}$ are for the reference field, and the method further comprises comparing the calculated field parameters with those measured during the treatment delivery.

In some embodiments of the method of validation, the reference field used for calculation is rectangular, centered at the fiber center and wide enough to cover all the scintillating optical fibers.

In some embodiments of the method of validation, $I_+$ and $I_-$ are from the fluence pattern under verification, and $I_{N+}$ and $I_{N-}$ are from a previously measured reference error-free field, and the method further comprises comparing the optical energy readings obtained during the treatment delivery with the previously measured reference error-free field.

DRAWINGS

The embodiments herein will now be described, by way of example only, with reference to the following drawings, in which:

FIG. 8 is a schematic view of different multileaf collimator errors that were analyzed and monitored using an exemplary embodiment; and FIG. 9 shows a table listing validation results according to some embodiments.

DESCRIPTION OF VARIOUS EMBODIMENTS

Figure 1:
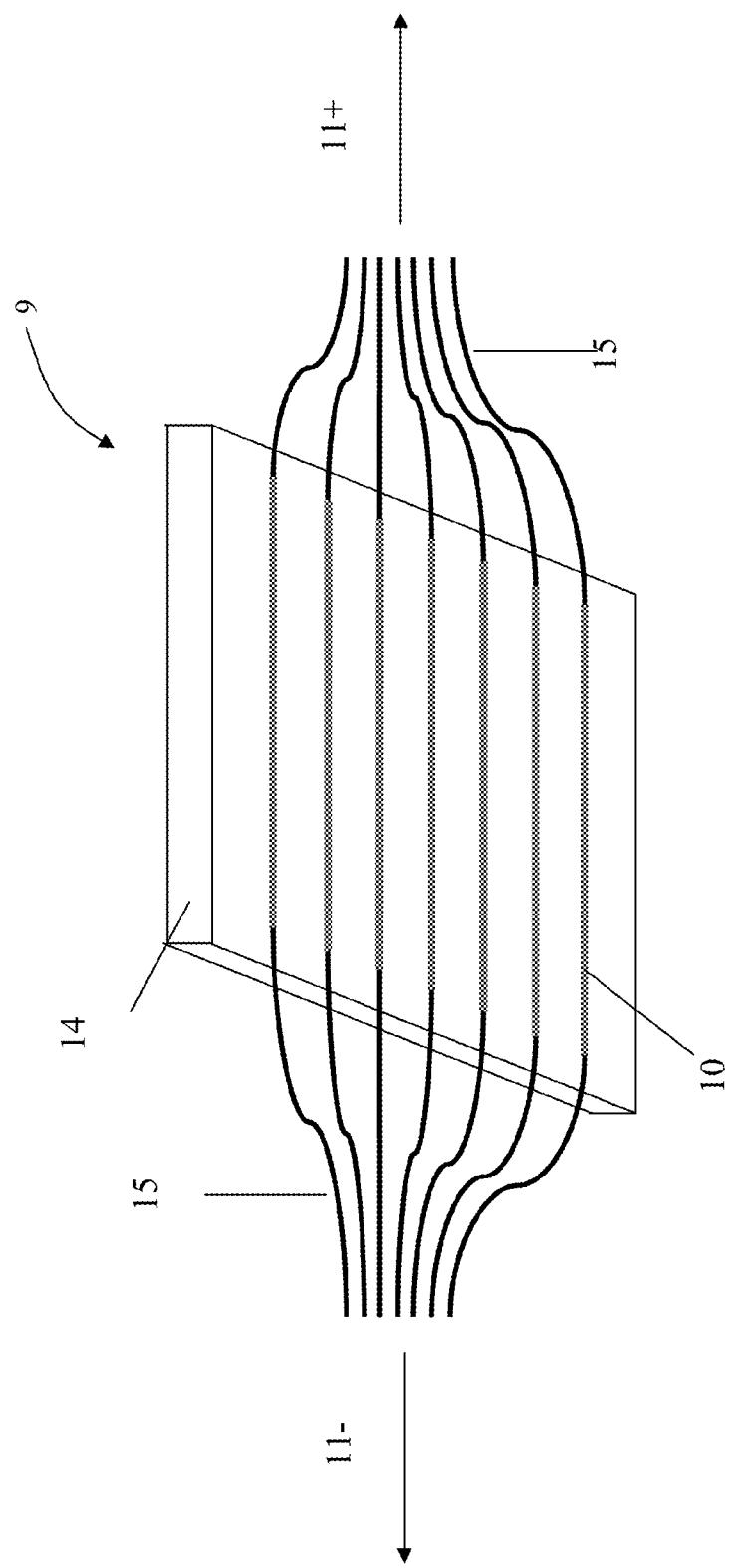
FIG. 1 is a schematic view of a radiation fluence monitoring detector according to one embodiment.

It will be appreciated that numerous specific details are set forth in order to provide a thorough understanding of the exemplary embodiments described herein. However, it will be understood by those of ordinary skill in the art that the embodiments described herein may be practiced without these specific details. In other instances, well-known methods, procedures and components have not been described in detail so as not to obscure the embodiments described herein.

Furthermore, this description is not to be considered as limiting the scope of the embodiments described herein in any way, but rather as merely describing the implementation of various embodiments as described herein.

While certain features have been illustrated and described herein, many modifications, substitutions, changes, and equivalents will now occur to those of ordinary skill in the art. It is, therefore, to be understood that the appended claims are intended to cover such modifications and changes as fall within the true spirit of the invention.

According to some embodiments, a fluence monitoring device as described herein includes a plurality of scintillating optical fibers sized and shaped to characterize an incident x-ray radiation pattern. Generally, at least some of the scintillating optical fibers are aligned along a direction of motion of a pair of leaves of a given multileaf collimator when the multileaf collimator is installed on a medical linear accelerator (also known as a "linac") operable to generate x-rays.

The scintillating optical fibers generate a light output at each end thereof, with the light output dependant of the incident radiation pattern. The ends of the scintillating optical fibers are each coupled to an optical fiber in order to guide the light emitted by the scintillating fibers to a photo-detector where it can be processed to determine the actual pattern of the incident radiation.

In some embodiments, the fluence monitoring device includes a phantom material (such as a thin slab of plastic or other material that is equivalent to the composition of the scintillating optical fibers) located in the vicinity of an accessory tray of the medical linear accelerator, with the scintillating optical fibers embedded in the phantom material. In some embodiments, both the scintillating fiber length and the phantom slab area are larger than the maximal cross-sectional area of the ionizing radiation beam at the height of the accessory tray of the medical linear accelerator (to accommodate beams of all sizes).

In some embodiments, the scintillating optical fibers are long enough to span the maximum leaf span (e.g. the gap between opposing leaves) of the multileaf collimator.

In some cases, each scintillating optical fibers may be arranged parallel to the direction of motion of the leaves and positioned underneath a pair of leaves of the multileaf collimator.

In some embodiments, the total number of scintillating optical fibers is equivalent to the number of leaf pairs in the multi-leaf collimator. In other embodiments, greater or lesser numbers of scintillating optical fibers may be used.

Generally, the optical fibers are used to collect the light output coming from both ends of each scintillating optical fiber. Thus two collection optical fibers are generally used for each scintillating optical fiber.

In some embodiments, the fluence monitoring device has a photo-detector that converts the optical energy transmitted by the optical fibers to electric signals. These electrical signals may then be interpreted to determine actual x-ray radiation pattern information. This actual radiation pattern information may then be compared to the expected radiation pattern to be delivered by the medical linear accelerator to determine how closely the actual radiation pattern matches the expected radiation pattern.

Also generally described herein is a theoretical model for predicting the optical energy produced by scintillating optical fibers and collected at each end thereof by collection optical fibers as a function of the incident x-ray radiation pattern.

Also generally described herein are methods of calibrating a fluence monitoring detector that uses long scintillating optical fibers to generate optical energy in response to x-ray radiation patterns incident on the scintillating optical fibers.

Also generally described herein are two methods of validation of the incident x-ray radiation pattern on scintillating optical fiber arrays. The first validation method compares the predicted optical energy readings with those readings measured during the actual treatment delivery. The second validation method compares the optical energy readings obtained during the treatment delivery with previously measured optical energy readings obtained from an error-free delivery.

Generally, some embodiments herein relate to a fluence monitoring device that makes use of scintillating optical fibers. In some embodiments, the scintillating optical fibers can be made thin enough so that one long scintillating optical fiber can monitor the fluence pattern associated to one leaf pair of a given multileaf collimator.

Turning now to FIG. 1, illustrated therein is a fluence monitoring detector 9 according to one embodiment. As shown, the fluence monitoring detector 9 includes a plurality of scintillating fibers 10 embedded in a phantom slab 14. Collection optical fibers 15 (e.g. clear or non-scintillating) are coupled to the ends of the scintillating fibers 10 in order for the emitted light 11+ and 11− from both the opposing ends of the scintillating fibers 10 be collected by a photo-detector 21.

The phantom slab 14 can be made of a material (e.g. common plastics) with properties relative to radiation that are similar to the material used in the scintillating optical fibers 10 (which may also be made of a plastic). Accordingly, with the scintillating optical fibers 10 embedded in a phantom slab 14 with similar material properties, the radiation beam perturbation tends to be minimized.

Figure 2:
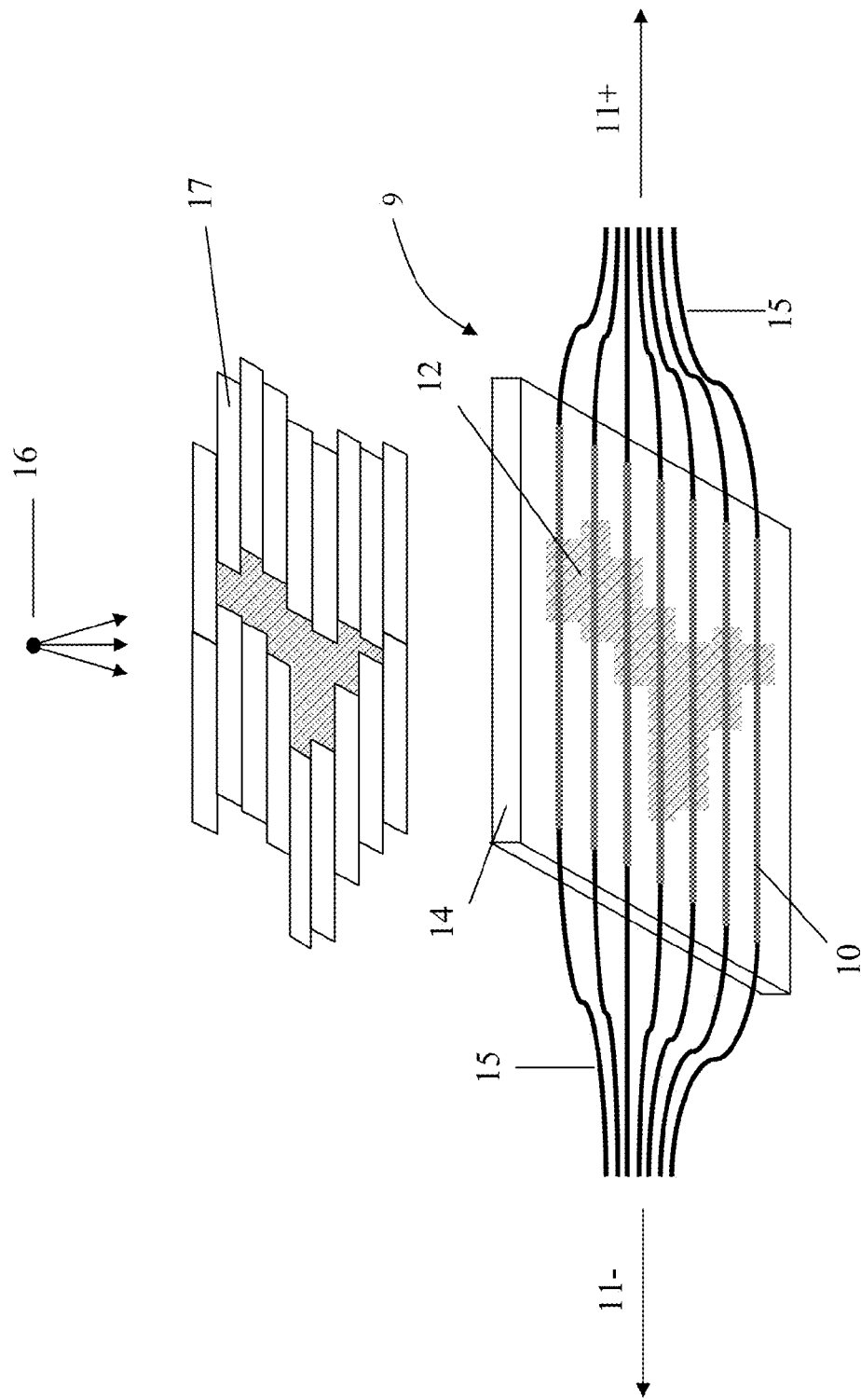
FIG. 2 is a schematic view of the fluence monitoring detector of FIG. 1 in position with a radiation source and a multileaf collimator according to some embodiments.

FIG. 2 shows the fluence monitoring detector 9 of FIG. 1 mounted in position relative to a multileaf collimator 17 and an x-ray radiation source (indicated schematically as 16) of a radiation delivery system. In particular, as shown the multileaf collimator 17 is positioned between the x-ray radiation source 16 and the fluence monitoring detector 9 (e.g. the scintillating optical fibers 10 are located on the opposite side of the multileaf collimator 17 from the x-ray radiation source 16).

In-use (e.g. during treatment), the scintillating optical fibers 10 and phantom slab 14 of the fluence monitoring detector 9 are irradiated by a fluence pattern 12 from the x-ray radiation source 16 (as modified by the multileaf collimator 17). The actual size and shape of the fluence pattern 12 will depend on the position of the leaves of the multileaf collimator 17, as well as the distance D1 between the x-ray radiation source 16 and the multileaf collimator 17, and the distance D2 between the x-ray radiation source 16 and the fluence monitoring detector 9.

Figure 3:
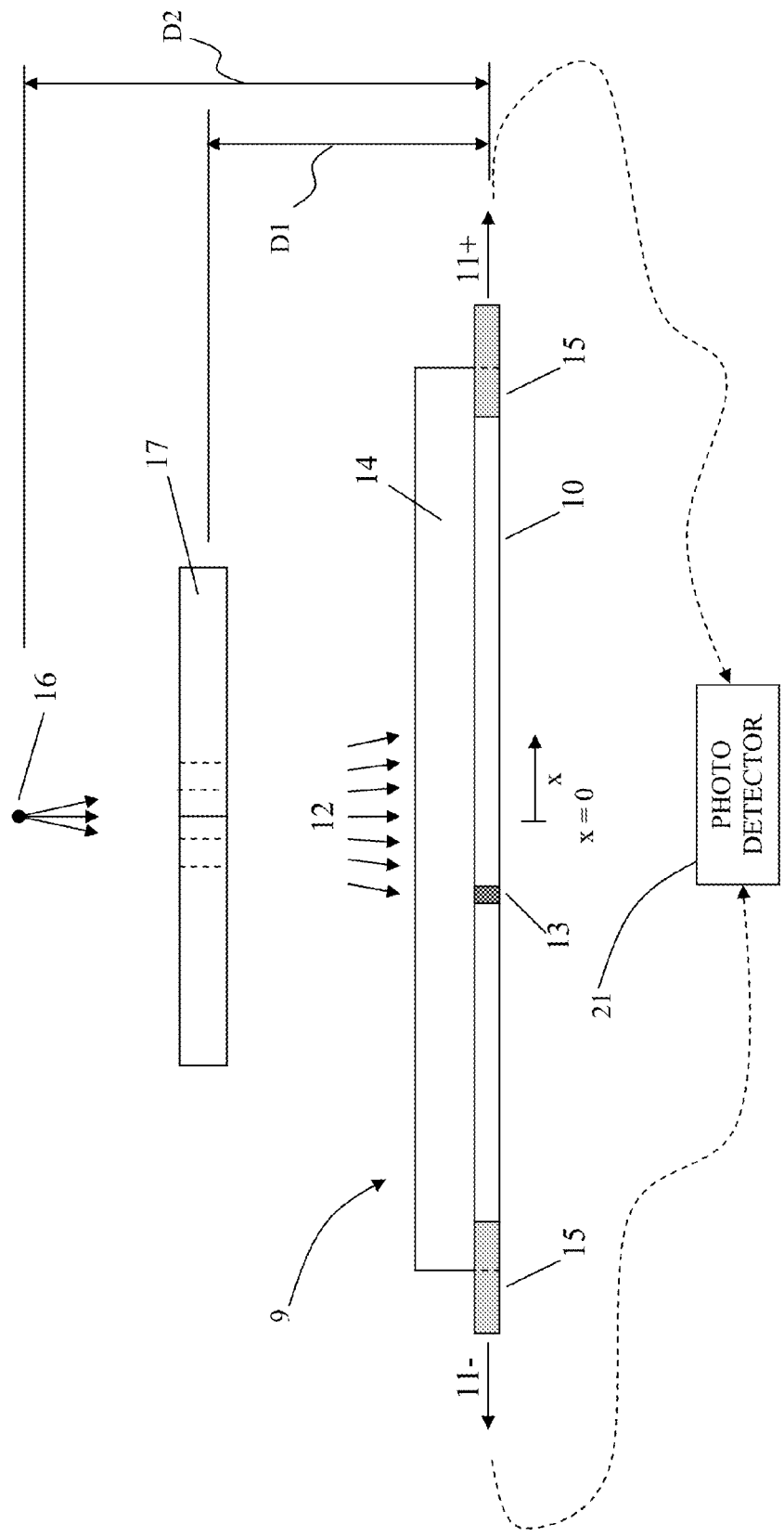
FIG. 3 is a schematic side view of the radiation source, multileaf collimator and fluence monitoring detector of FIG. 2.

FIG. 3 shows the same setup as in FIG. 2, viewed from the side. Those skilled in the art will recognize that the distance D2 between the schematized x-ray radiation source 16 and the plane of the scintillating optical fibers 10 should be small enough so that any given patient can be treated with radiation from the x-ray radiation source 16 while the fluence monitoring detector 9 is in place (e.g. between the multileaf collimator 17 and the patient). In particular, in some embodiments the fluence monitoring detector 9 and multileaf collimator 17 should be as close as possible.

Figure 4:
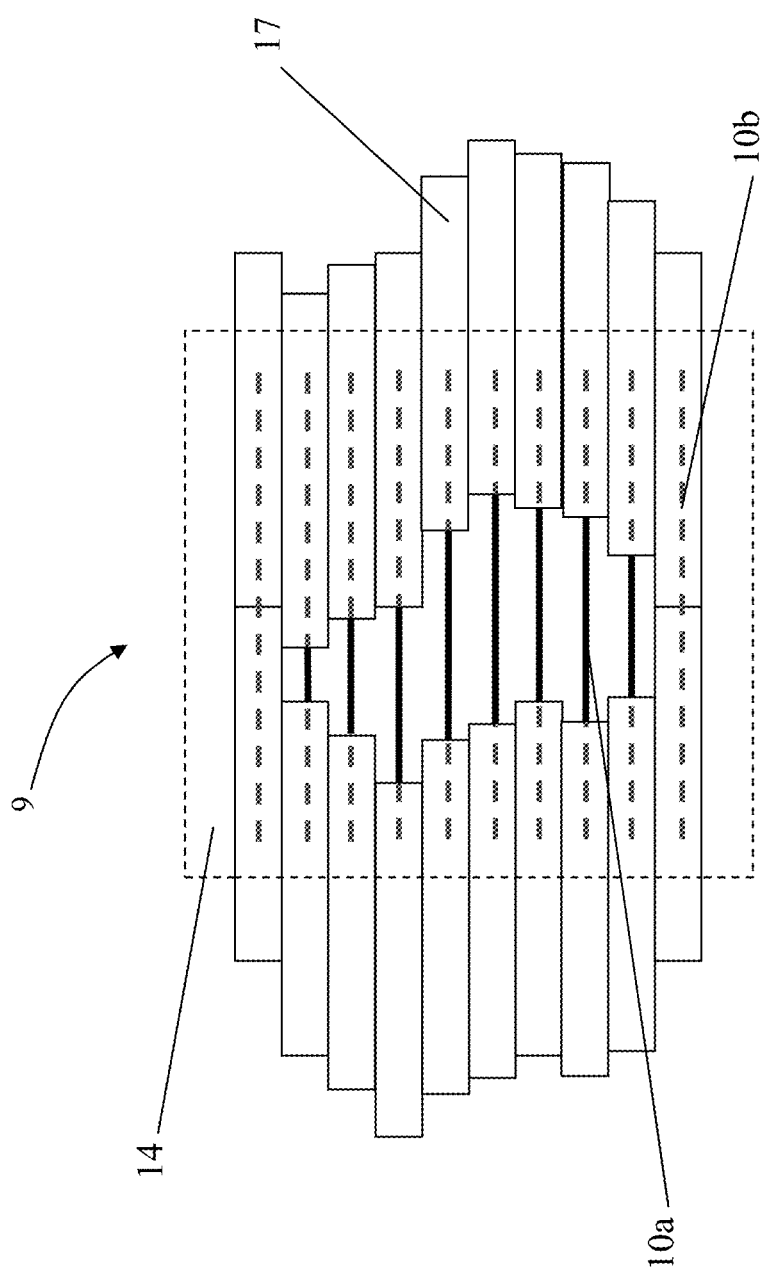
FIG. 4 is a schematic view of the multileaf collimator and fluence monitoring detector of FIGS. 2 and 3, viewed from the perspective of the radiation source.

FIG. 4 shows the multileaf collimator 17 assembly and the fluence monitoring detector 9, as viewed by the x-ray radiation source 16. As a matter of perspective, a visible portion 10a of the scintillating optical fibers 10 is visible from the x-ray radiation source 16 (represented by thick lines), while a masked portion 10b of the scintillating optical fibers 10 is masked by the multileaf collimator 17 (represented as dotted lines).

In order for the fluence pattern to be verified, each pair of leaves in the multileaf collimator 17 may be associated with a particular scintillating optical fiber 10. Those skilled in the art will understand that the number of leaf pairs in a typical multileaf collimator assembly may be greater that the number shown in the drawings. However, for clarity, the figures and embodiments herein show and describe only a limited number of leaf pairs in the multileaf collimator 17, and hence a limited number of scintillating optical fibers 10.

Also described herein is a model that predicts the optical energy produced by the scintillating optical fibers 10. From this model and following the irradiation of a long scintillating fiber 10, as shown schematically in FIG. 3, the light collected by each end (+/−) of the fiber (i.e. $I_+$ and $I_-$) is determined by the integration of the contribution of each infinitesimal element 13 on the scintillating optical fibers 10:

$$I_\pm = C_\pm \cdot \int_{-\frac{L}{2}}^{\frac{L}{2}} \kappa(x) \cdot \Phi_i(x) \cdot e^{\pm \lambda(x)} \cdot dx \quad (1)$$

where $\kappa(x)$ represents the scintillation efficiency (i.e. the number of scintillation photons emitted per incident fluence particles), $\Phi_i(x)$ represents the linear fluence across the fiber. (m$^{-1}$), $\lambda(x)$ accounts for the differential light attenuation along the optical fiber, $C_\pm$ represent the light losses due to the optical coupling to the photo-detector and L represent the fiber length. As shown, the position "x=0" has been defined as the center of the fibers 10 with respect to the radiation source 16.

Also described herein is a method of calibrating a fluence monitoring detector (e.g. the fluence monitoring detector 9) that includes long scintillating optical fibers (e.g. optical fibers 10) that generate optical energy in response to the incident radiation pattern. As used herein, "calibrating" generally refers to the determination of a scintillation efficiency ($\kappa(x)$) and a differential light attenuation ($\lambda(x)$) for all positions on a particular scintillating optical fiber or array of scintillating optical fibers.

Figure 5:
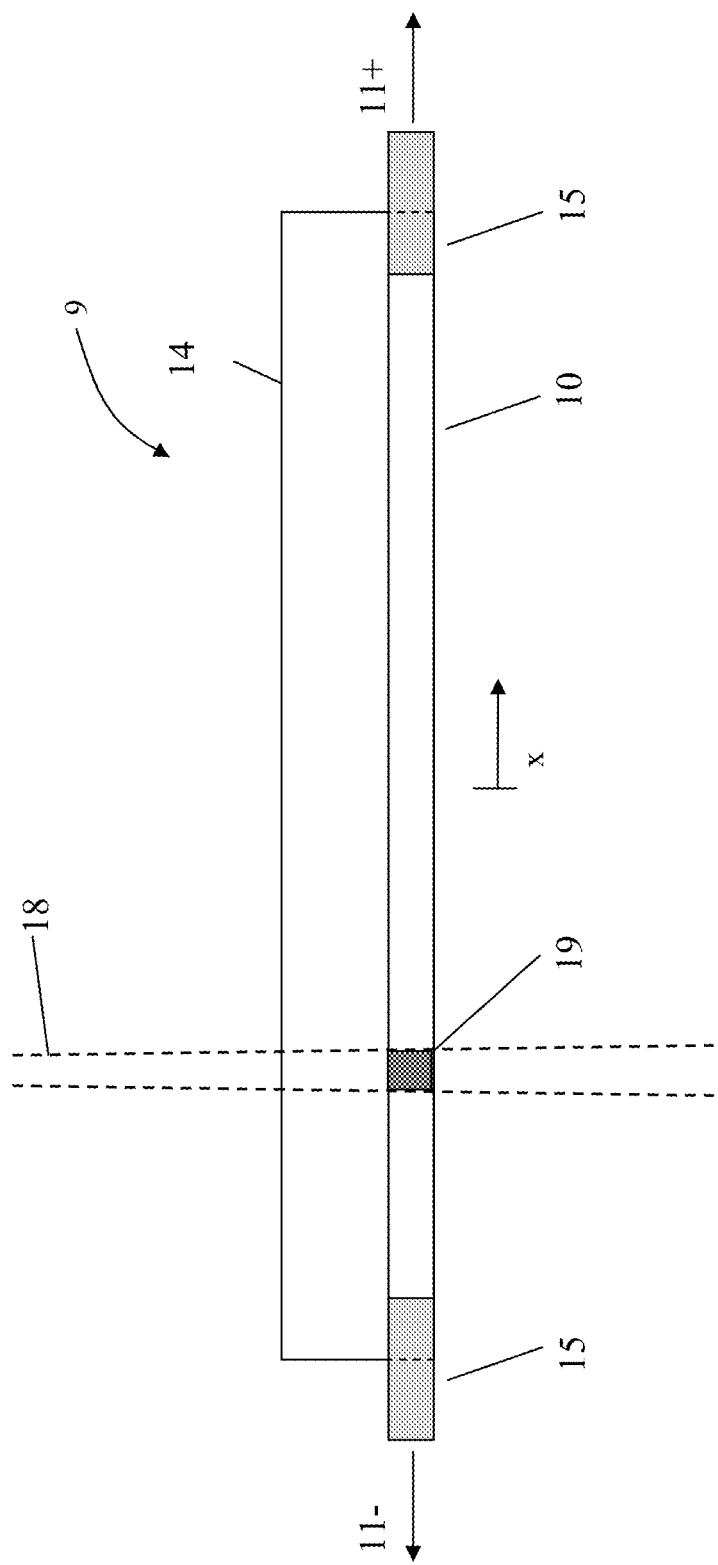
FIG. 5 is a schematic side view of a radiation fluence monitoring detector irradiated with a radiation field for calibration according to one embodiment.
Figure 6:
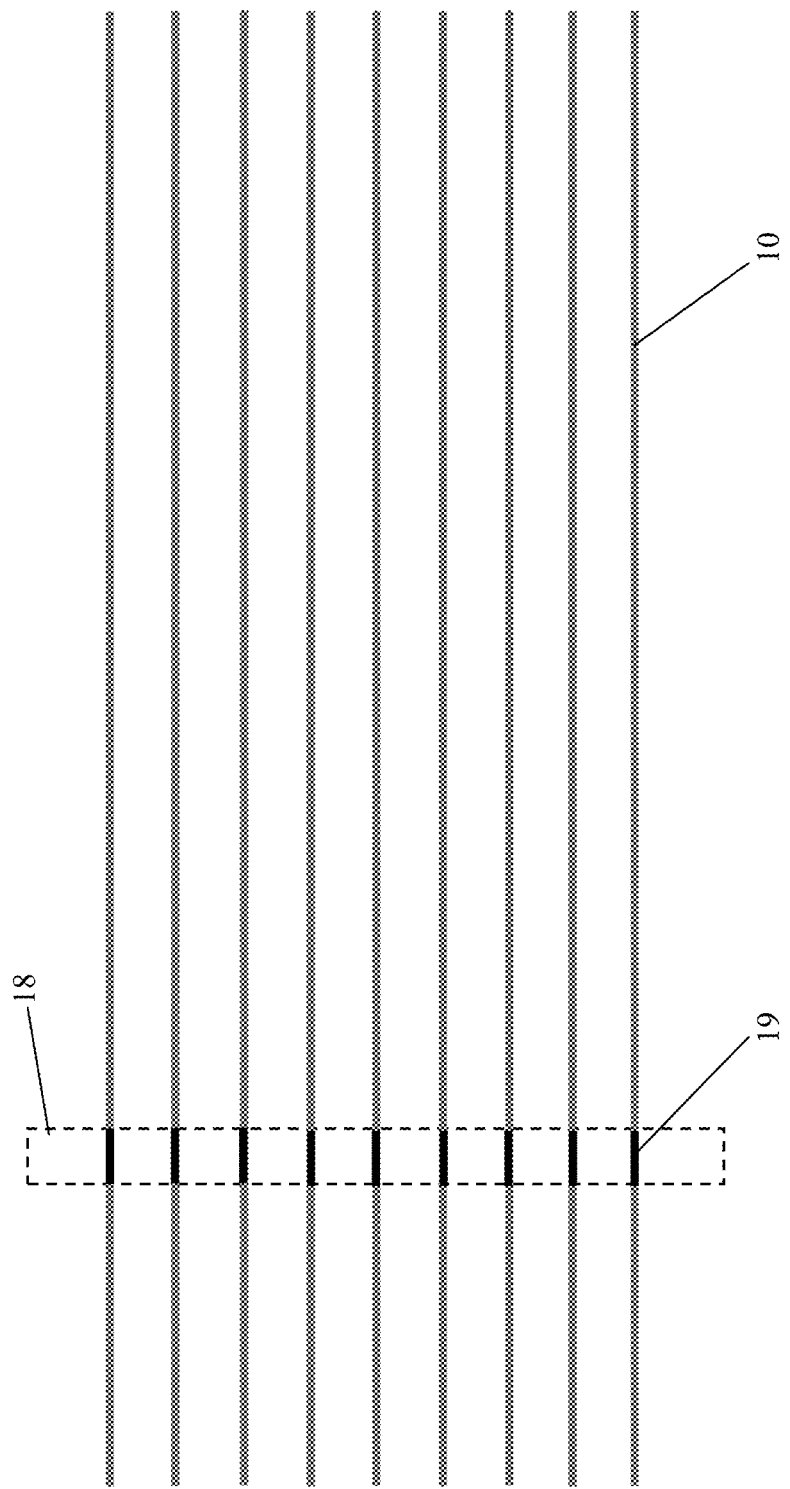
FIG. 6 is a schematic top view of the radiation fluence monitoring detector of FIG. 5.

As seen in FIG. 5 (side view) and FIG. 6 (top view), the calibration may be done using a narrow rectangular x-ray radiation field 18 incident on the array of scintillating optical fibers 10. The scintillating optical fibers 10 are set perpendicular to the rectangular x-ray field 18 and the x-ray radiation field 18 is wide enough (e.g. 30 to 40 cm) to enable simultaneous irradiation of all the fibers 10.

It may be assumed that the irradiated portion 19 of each scintillating optical fiber 10 has a length d and is defined around its central position $x_f$. The integral mean value theorem of Equation (1) above can then be used to find:

$$I_\pm = C_\pm \cdot \kappa(x_0) \cdot \Phi_{int}(x_0) \cdot e^{\pm \lambda(x_0)} \quad x_0 \in \left[x_f - \frac{d}{2}, x_f + \frac{d}{2}\right] \quad (2)$$

where d represents the effective rectangular field width (that is, the width beyond which the radiation fluence is considered to be negligible) and $x_0$ represents the effective point of measure, as defined by the integral mean value theorem; $C_\pm$, $\kappa$, $\Phi_{int}$ and $\lambda$ are defined as before. As d is small, we can consider that $x_0$ will be equivalent to $x_f$. This assumption is corroborated by the fact that 1) $\kappa$ is approximately constant along the interval, 2) $\Phi_I$ is symmetrical with respect to $x_f$ and 3) the variation attributable to $\lambda$ is small along the interval. Having deduced that $x_0 \approx x_f$ the value of $\kappa(x)$ and $\lambda(x)$ can be computed at the position $x_f$ on the fiber:

$$\mu(x_f) = \frac{1}{2} \ln\left(\frac{I_+(x_f)}{I_-(x_f)} \cdot \frac{I_-(0)}{I_+(0)}\right) \quad (3)$$

$$\frac{\kappa(x_f)}{\kappa(0)} = \sqrt{\frac{I_+(x_f)}{I_+(0)} \cdot \frac{I_-(x_f)}{I_-(0)}} \quad (4)$$

To complete the calibration, one can apply the above-mentioned rectangular x-ray radiation field over the entire scintillating optical fiber length (e.g. in a plurality of irradiations) in order to calculate $\mu(x)$ and $\kappa(x)$ for all positions along the fiber.

Also provided herein are two exemplary methods of validation of the incident radiation pattern on an array of scintillating optical fibers (e.g. scintillating optical fibers 10). These validation methods use comparison and calculation of field parameters, namely the central position of the radiation interaction on the scintillation optical fiber ($x_c$) and the integral of the fluence passing through the scintillating optical fiber ($\phi_{int}$). These field parameters are calculated as follow:

$$x_c = \frac{1}{2\mu} \ln\left(\frac{I_+}{I_{N+}} \cdot \frac{I_{N-}}{I_-}\right) \quad (5)$$

$$\Phi_{int} = \Phi_{intN} \sqrt{\frac{I_+}{I_{N+}} \cdot \frac{I_-}{I_{N-}}} \quad (6)$$

where $I_+$, $I_-$, $I_{N+}$ and $I_{N-}$ are defined by Equation 1, both $I_+$ and $I_-$ for the field under analysis and both $I_{N+}$ and $I_{N-}$ for the reference field. The constant $\mu$ represents the mean attenuation coefficient of the scintillating optical fibers.

The first validation method compares the calculated field parameters (using Equations 5 and 6) with those measured during the treatment delivery. The reference field used for calculation is usually rectangular, centered at the fiber center (e.g. x=0) and wide enough to cover all the scintillating optical fibers.

The theoretical fluence pattern can be calculated using independent fluence calculation software (e.g. treatment planning software) or measured with a dosimeter for both the treatment field and the reference field. From this fluence pattern, the value obtained for the scintillation efficiency ($\kappa(x)$), and the differential light attenuation ($\lambda(x)$) from the calibration of the detector, the theoretical field parameters can be calculated. These calculated field parameters can then be compared during the treatment delivery of a particular patient to the value measured by the fluence monitoring detector 9 for $x_c$ and $\phi_{int}$.

The second validation method compares the optical energy readings obtained during the treatment delivery with the previously measured optical energy readings obtained from a reference delivery. This reference fluence pattern may be asserted error-free by an alternate validation method, for example, using the first validation method described herein or a quality assurance test performed experimentally on the treatment plan.

To apply this second validation method for a given fluence pattern, one may compute the field parameters ($x_c$ and $\phi_{int}$) with Equations 5 and 6, using both $I_+$ and $I_-$ from the fluence pattern under verification, and both $I_{N+}$ and $I_{N-}$ from the reference error-free field. If the field under examination is free of delivery errors, the value measured for $x_c$ should be 0 and the value measured for $\phi_{int}$ should be 1, according to Equations 5 and 6.

Figure 7:
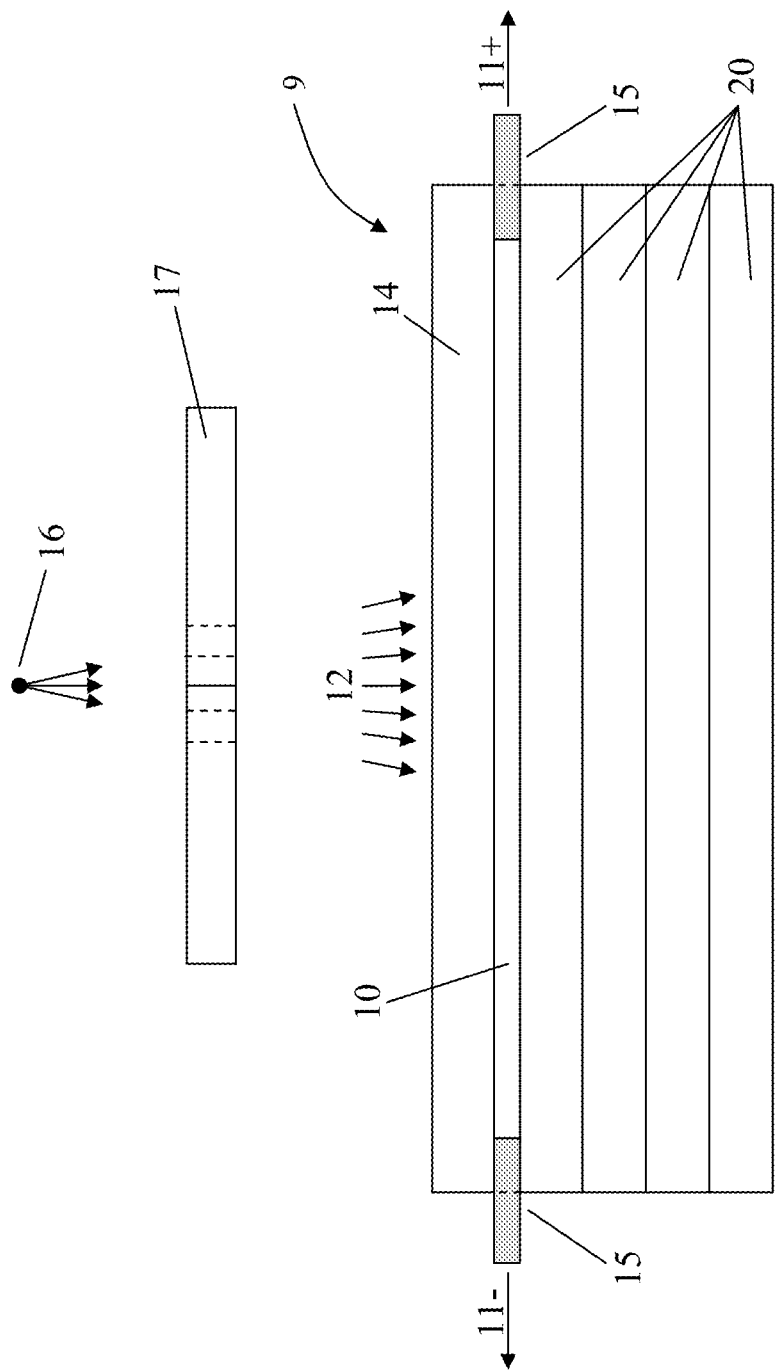
FIG. 7 is a schematic view of an embodiment wherein several water-equivalent slabs are added under the radiation fluence monitoring detector of FIG. 1 to facilitate fluence calculation.

Also described generally herein are performance measurements of an exemplary embodiment of the fluence monitoring detector 9. In this embodiment (as shown in FIG. 7), the an array of scintillating optical fibers 10 is located at the isocenter of a treatment linear accelerator (e.g. 100 cm from the x-ray radiation source 16), with a phantom slab 14 made of a material equivalent to solid water and which is 2 cm thick. Also included are several solid water slabs 20 located under the scintillating fiber array 10 phantom slab 14.

These additional slabs 20 are added to enable consistent calculation of the incident fluence pattern by the treatment planning software used (in this embodiment, Pinnacle$^3$ 8.0 m, a radiation therapy planning system offered by Philips, was used).

To evaluate the performance of the embodiment shown in FIG. 7, randomly generated errors where included in fourteen step-and-shoot IMRT fields extracted from an oropharyngeal head and neck cancer case. Those random errors were classified as two types: 1) single leaf errors (SLE), in which only an individual leaf in the multileaf collimator 17 is moved from its original position by a certain amount and 2) pair translation errors (PTE), in which two associated leaves forming a pair in the multileaf collimator 17 are moved in the same direction, to preserve the opening length (e.g. the gap) between the two.

SLE is expected to modify the radiation output more significantly than PTE. However PTE would produce a systematic shift of position of the radiation field.

The impact of leaf bank errors were also explored. A field in which all the leaves in one of the leaf bank underwent a SLE were classified as leaf bank error (LBE), while a field in which the two leaf banks underwent the same parallel displacement (similar to a PTE) were classified as field translation error (FTE). All described errors are illustrated generally in FIG. 8.

These erroneous fields (in which a random leaf error was included) were verified using the second validation method described above. The correct field (with no random error included) was used as normalization field. The results of this validation are presented in table 1 as shown in FIG. 9. The deviation between the measured and expected value of $x_c$ was quantified as a number of standard deviations (SD) attributable to statistical variation (following a Poissonnian model). The deviation between the measured and expected value of $\phi_{int}$ was quantified in percent of the total expected integral fluence. As one can see, the deviation observed for unmodified (error-free) leaves is representative of the intrinsic variation of the field parameters.

Generally, some embodiments as described herein cannot detect leaf errors inferior to these intrinsic statistical variations. Setting the detection threshold (above which an error can be detected) to 3 standard deviations for $x_c$ and 0.5% for $\phi_{int}$, one can see that any SLE, LBE or FTE of 1 mm or more or any PTE of 2 mm or more can be identified by the embodiments as described herein.

The embodiments herein generally enables in-use (e.g. during treatment) verification of any radiotherapy treatment that makes use of multileaf collimators. The embodiments as described herein also make use of the significant attenuation of scintillating optical fibers to provide monitoring of the incident fluence using two independent field parameters.

Real-time validation of the incident fluence can be made by comparing the calculated field parameters (using an independent fluence calculator and fiber calibration) to the measured ones. This real-time validation can also be conducted by computing the field parameters using an error-free delivery as the reference metric.

While certain features have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A fluence monitoring detector for use with a multileaf collimator on a radiotherapy machine having an x-ray radiation source, the fluence monitoring detector comprising:
   a) a plurality of scintillating optical fibers, each scintillating optical fiber configured to generate a light output at each end thereof in response to incident radiation pattern thereon from the radiation source and multileaf collimator;
   b) a plurality of collection optical fibers coupled to the opposing ends of the scintillating optical fibers and operable to collect the light output coming from both ends of each scintillating optical fiber; and
   c) a photo-detector coupled to the collection optical fibers and operable to convert optical energy transmitted by the collection optical fibers to electric signals for determining actual radiation pattern information.

2. The fluence monitoring detector of claim 1, wherein the scintillating fibers are embedded in a phantom slab.

3. The fluence monitoring detector of claim 2, wherein the phantom slab is made of a material with properties relative to x-ray radiation that are similar to the material used in the scintillating optical fibers.

4. The fluence monitoring detector of claim 2, wherein the phantom slab is made thin enough as to minimize the attenuation of the x-ray radiation beam.

5. The fluence monitoring detector of claim 2, wherein both the scintillating fiber length and the phantom slab area are large enough to span the maximum leaf span of the multileaf collimator.

6. The fluence monitoring detector of claim 1, wherein each pair of leaves in the multileaf collimator is associated with a particular scintillating optical fiber.

7. The fluence monitoring detector of claim 1, wherein each scintillating optical fibers is arranged parallel to a direction of motion of the leaves of the multileaf collimator.

8. The fluence monitoring detector of claim 1, wherein each scintillating optical fiber is positioned underneath a pair of leaves of the multileaf collimator.

9. The fluence monitoring detector of claim 1, wherein each scintillating optical fiber has a length selected so as to span the maximum leaf span of a pair of leaves in the multileaf collimator.

10. The fluence monitoring detector of claim 1, wherein the scintillating optical fibers are located on the opposite side of the multileaf collimator from the x-ray radiation source.

11. The fluence monitoring detector of claim 1, wherein the scintillating optical fibers are close enough to the opposite side of the multileaf collimator from the radiation source as to keep sufficient clearance between the patient and the scintillating optical fibers.

12. The fluence monitoring detector of claim 1, wherein the scintillating optical fibers are thin enough so that one scintillating optical fiber can monitor the fluence pattern associated with one leaf pair of the multileaf collimator.

13. The fluence monitoring detector of claim 1, wherein the total number of scintillating optical fibers is equivalent to the number of leaf pairs in the multi-leaf collimator.

14. The fluence monitoring detector of claim 1, wherein the light collected by each end of each scintillating optical fiber is determined by the integration of the contribution of each infinitesimal element along that fiber according to the following equation:

$$I_\pm = C_\pm \cdot \int_{-\frac{L}{2}}^{\frac{L}{2}} \kappa(x) \cdot \Phi_l(x) \cdot e^{\pm \lambda(x)} \cdot dx$$

where $\kappa(x)$ represents the scintillation efficiency, $\Phi_l(x)$ represents the linear fluence across the fiber (m$^{-1}$), $\lambda(x)$ accounts for the differential light attenuation along the optical fiber, $C_\pm$ represent the light losses due to the optical coupling to the photo-detector and L represent the fiber length.

15. The fluence monitoring detector of claim 1, wherein the photo-detector is further configured to determine actual radiation pattern information, and compare this actual radiation pattern information to the expected radiation pattern to determine how closely the actual radiation pattern matches the expected radiation pattern.

16. The fluence monitoring detector of claim 1, further comprising several solid slabs located under the scintillating fiber array and the phantom slab.

17. A method of calibrating a fluence monitoring detector that has scintillating optical fibers for use with a multileaf collimator on a radiotherapy machine having an x-ray radiation source, the method comprising:
using a narrow rectangular x-ray radiation field incident on the scintillating optical fibers, with the scintillating optical fibers set perpendicular to the rectangular field and the x-ray radiation field is wide enough to enable simultaneous irradiation of all the fibers; and
determining the light collected by each end of the scintillating fibers according to the following equation:

$$I_\pm = C_\pm \cdot \kappa(x_0) \cdot \Phi_{int}(x_0) \cdot e^{\pm \lambda(x_0)} \quad x_0 \in \left[x_f - \frac{d}{2}, x_f + \frac{d}{2}\right]$$

wherein d represents the effective rectangular field width and $x_0$ represent the effective point of measure, as defined by the integral mean value theorem, $\kappa(x)$ represents the scintillation efficiency, $\Phi_l(x)$ represents the linear fluence across the fiber (m$^{-1}$), $\lambda(x)$ accounts for the differential light attenuation along the optical fiber, and $C_\pm$ represent the light losses due to the optical coupling to the photo-detector.

18. The method of claim 17, further comprising determining the values of $\kappa(x)$ and $\lambda(x)$ at the position $x_f$ on the fibers according to the following equations:

$$\mu(x_f) = \frac{1}{2} \ln\left(\frac{I_+(x_f)}{I_-(x_f)} \cdot \frac{I_-(0)}{I_+(0)}\right)$$

$$\frac{\kappa(x_f)}{\kappa(0)} = \sqrt{\frac{I_+(x_f)}{I_+(0)} \cdot \frac{I_-(x_f)}{I_-(0)}}.$$

19. The method of claim 18, further comprising applying the rectangular x-ray radiation field over the entire scintillating optical fiber length in a plurality of irradiations in order to calculate $\mu(x)$ and $\kappa(x)$ for all positions along the fiber.

20. A method of validation of an incident radiation pattern on an array of scintillating optical fibers for use with a multileaf collimator on a radiotherapy machine having an x-ray radiation source, comprising:
calculating the following field parameters: central position of the radiation interaction on the scintillation optical fiber ($x_c$) and the integral of the fluence passing through the scintillating optical fiber ($\phi_{int}$) according to the following equations:

$$x_c = \frac{1}{2\mu} \ln\left(\frac{I_+}{I_{N+}} \cdot \frac{I_{N-}}{I_-}\right)$$

$$\Phi_{int} = \Phi_{intN} \sqrt{\frac{I_+}{I_{N+}} \cdot \frac{I_-}{I_{N-}}}$$

wherein $\mu$ is a constant that represents the mean attenuation coefficient of the scintillating optical fibers, and wherein $I_+$, $I_-$, $I_{N+}$ and $I_{N-}$ are defined by the following equation:

$$I_\pm = C_\pm \cdot \int_{-\frac{L}{2}}^{\frac{L}{2}} \kappa(x) \cdot \Phi_l(x) \cdot e^{\pm \lambda(x)} \cdot dx$$

where $\kappa(x)$ represents the scintillation efficiency, $\Phi_l(x)$ represents the linear fluence across the fiber (m$^{-1}$), $\lambda(x)$ accounts for the differential light attenuation along the optical fiber, $C_\pm$ represent the light losses due to the optical coupling to the photo-detector and L represent the fiber length.

21. The method of validation of claim 20, wherein $I_+$ and $I_-$ are for the field under analysis and $I_{N+}$ and $I_{N-}$ are for the reference field, and further comprising comparing the calculated field parameters with those measured during the treatment delivery.

22. The method of validation of claim 21, wherein the reference field used for calculation is rectangular, centered at the fiber center and wide enough to cover all the scintillating optical fibers.

23. The method of validation of claim 20, wherein $I_+$ and $I_-$ are from the fluence pattern under verification, and $I_{N+}$ and $I_{N-}$ are from a previously measured reference error-free field, and further comprising comparing the optical energy readings obtained during the treatment delivery with the previously measured reference error-free field.

* * * * *